(12) United States Patent
Shavit et al.

(10) Patent No.: US 10,328,015 B2
(45) Date of Patent: Jun. 25, 2019

(54) FRAGRANCE RELEASING COMPOSITIONS

(71) Applicant: AMKIRI LTD., Tel Aviv (IL)

(72) Inventors: Shoval Shavit, Tel Aviv (IL); Aliza Shavit, Tel Aviv (IL)

(73) Assignee: AMKIRI LTD., Tel Aviv (IL)

( * ) Notice: Subject to any disclaimer, the term of this patent is extended or adjusted under 35 U.S.C. 154(b) by 0 days.

(21) Appl. No.: 15/915,156

(22) Filed: Mar. 8, 2018

(65) Prior Publication Data
US 2018/0193246 A1 Jul. 12, 2018

Related U.S. Application Data

(63) Continuation-in-part of application No. 15/112,219, filed as application No. PCT/IL2015/050088 on Jan. 22, 2015, now Pat. No. 9,943,469.

(60) Provisional application No. 61/930,539, filed on Jan. 23, 2014.

(51) Int. Cl.
| | | |
|---|---|---|
| *A61L 9/04* | (2006.01) | |
| *A61K 8/00* | (2006.01) | |
| *A61K 8/81* | (2006.01) | |
| *C11B 9/00* | (2006.01) | |
| *A61Q 13/00* | (2006.01) | |
| *A61K 8/34* | (2006.01) | |
| *A61K 8/29* | (2006.01) | |
| *A61K 8/25* | (2006.01) | |
| *A61K 8/26* | (2006.01) | |
| *A61K 8/88* | (2006.01) | |
| *A61K 8/20* | (2006.01) | |

(52) U.S. Cl.
CPC ............. *A61K 8/8152* (2013.01); *A61K 8/20* (2013.01); *A61K 8/25* (2013.01); *A61K 8/26* (2013.01); *A61K 8/29* (2013.01); *A61K 8/34* (2013.01); *A61K 8/345* (2013.01); *A61K 8/88* (2013.01); *A61Q 13/00* (2013.01); *C11B 9/00* (2013.01)

(58) Field of Classification Search
CPC .......... A61K 8/8152; A61K 8/29; A61K 8/25; A61K 8/345; A61K 8/34; A61Q 13/00; C11B 9/00

USPC ........................................................ 512/4, 1
See application file for complete search history.

(56) References Cited

U.S. PATENT DOCUMENTS

| | | |
|---|---|---|
| 6,143,353 A | 11/2000 | Oshlack et al. |
| 6,454,842 B1 | 9/2002 | Vernardakis et al. |
| 8,921,303 B1 | 12/2014 | Lull et al. |
| 2003/0076393 A1 | 4/2003 | Lee |
| 2005/0137326 A1 | 6/2005 | Sanfilippo |
| 2005/0244349 A1 | 11/2005 | Chaudhuri et al. |
| 2006/0287205 A1 | 12/2006 | Popplewell et al. |
| 2008/0115796 A1 | 5/2008 | Montanari et al. |
| 2008/0153736 A1 | 6/2008 | Elder et al. |
| 2010/0047202 A1* | 2/2010 | Goddinger ............. A61K 8/731 424/70.12 |
| 2013/0171078 A1* | 7/2013 | Lawson ................... A61Q 1/06 424/59 |
| 2016/0287205 A1 | 10/2016 | Zou et al. |

FOREIGN PATENT DOCUMENTS

| | | |
|---|---|---|
| DE | 1913569 A1 | 10/1969 |
| DE | 102010049642 A1 | 1/2012 |
| EP | 0568035 A2 | 11/1993 |
| JP | 2003064393 A | 3/2003 |
| WO | 1989004673 A1 | 6/1989 |
| WO | 2005070371 A2 | 8/2005 |
| WO | 2008115961 A2 | 9/2008 |
| WO | 2009064739 A1 | 5/2009 |
| WO | 2014011860 A2 | 1/2014 |

OTHER PUBLICATIONS

Water-based Polyurethane and Acrylate Dispersions for Flexible Substrates, 2011, p. 5, Retrieved <https://docplayer.net/21787533-Water-based-polyurethane-and-acrylate-dispersions-forflexiblesubstrates.html>, Accessed Dec. 5, 2018.
Acrysol RM-2020 NPR Rheology Modifier, Mar. 2013, pp. 1-2.

\* cited by examiner

*Primary Examiner* — Jessica Whiteley
(74) *Attorney, Agent, or Firm* — The Roy Gross Law Firm, LLC; Roy Gross

(57) ABSTRACT

A composition having extended fragrance retention capability including an acrylic polymer, to be applied a human body surface is provided. The composition can be applied by using a kit which includes means for applying the fragrance releasing complex to the body surface.

16 Claims, No Drawings

FRAGRANCE RELEASING COMPOSITIONS

This Application is a continuation-in-part of U.S. patent application Ser. No. 15/112,219, filed Jul. 18, 2016, which is a national phase application of PCT Patent Application No. PCT/IL2015/050088, filed Jan. 22, 2015, which claims priority to U.S. Provisional Patent Application No. 61/930,539, filed Jan. 23, 2014. These applications are incorporated herein by reference in their entirety.

The invention, in some embodiments thereof, provides a composition and/or a fragrance-releasing complex.

BACKGROUND OF THE INVENTION

Since early human history, scents and fragrances have been used to modify body odor. They were obtained in raw form such as resins, gums or essential oils and derived from natural sources, such as the bark, roots, leaves and fruit of indigenous plants and trees. These raw materials were then diluted with water or other solvents and applied to the skin. In modern times, the chemical components responsible for the odor properties of these raw materials were isolated and identified.

Current day perfumery engages in combining various fragrance materials to obtain novel fragrance compositions with specific "characteristics".

In light of the advancements in chemical technology many fragrances are no longer derived from natural sources but are synthesized as highly pure fragrance raw materials (FRM). Furthermore, fragrances have been categorized into three "note" types based on their relative volatility; base, having the most long lasting aroma; middle having a medium volatility, and top notes being the most volatile. If used correctly the different note combinations can produce a "balanced fragrance" composition i.e. one which diffuses in a manner having an aesthetic pleasing effect.

In addition, fragrances have been grouped according to the odor they produce, by using both broad and specific descriptions. For example, "floral" is a term used for odors associated with flowers while the term "lilac" is more specific. Additional examples of descriptive terms include "rose", "floral", "green", "citrus", "spicy", "honey", and "musk".

Due to an uneven evaporation rate of the different components, the initial fragrance may be quite different from the aroma perceived several hours later. Several methods have been commonly employed to address this issue. One method is to "load up" on the perfume initially and rely on the natural evaporation rate to diminish the fragrance so as to reach a suitable level several hours later when the desired effect is required. Another method is to continually reapply small amounts of the perfume to the skin at short time intervals. However neither of these solutions overcomes the problem of the diminishing level of top and middle notes over time. In fact, base notes which are present over an extended period in light of their low volatility, begin to accumulate with each renewed appliance of perfume, with the possible outcome of overwhelming the other fragrance notes and negating the original fragrance balance.

Acrylic acid (prop-2-enoic acid) is an organic compound with the formula $CH_2=CHCO_2H$. It consists of a vinyl group connected directly to a carboxylic acid terminus and is the simplest unsaturated carboxylic acid. It is a colorless liquid with an acrid or tart smell. It is miscible with water, alcohols, ethers, and chloroform. It is used extensively in different forms and more than one billion kilograms are produced annually. Acrylic acid is produced from propene which is a byproduct of ethylene and gasoline production.

Acrylate polymers belong to a group of polymers which are commonly referred to as plastics. Some of their notable characteristics include transparency, resistance to breakage, and elasticity. They are also generally known as acrylics or polyacrylates. Acrylate polymers are formed from Acrylate monomers which are based on the structure of acrylic acid or are derivatives of acrylic acid, such as methyl methacrylate in which one vinyl hydrogen and the carboxylic acid hydrogen are both replaced by methyl groups, and acrylonitrile in which the carboxylic acid group is replaced by the related nitrile group.

Acrylic paint is a paint containing a pigment suspension in an acrylic polymer emulsion. It can be diluted with water, but becomes water-resistant when dry. Depending on the degree to which the paint is diluted with water, or modified with acrylic gels, media, or pastes, the finished acrylic painting can have unique characteristics not attainable with other media.

SUMMARY OF THE INVENTION

The invention, in some embodiments thereof, provides a composition and/or a fragrance-releasing complex.

According to an aspect of some embodiments of the present invention, there is provided a composition comprising: (i) aqueous solution, (ii) a fragrance; (iii) an acrylic polymer, (iv) a polymeric thickener, and (v) a pigment, wherein the acrylic polymer is present at a concentration from 20% to 60%, or, in some embodiments, from 20% to 40%, by total weight of the composition.

In some embodiments, the polymeric thickener comprises polysaccharide.

In some embodiments, the polymeric thickener is selected from the group consisting of: xanthan gum, gellan gum, welan gum, guar gum, a carob, a flour, or any combination thereof.

In some embodiments, the thickener is xanthan gum.

In some embodiments, the composition further comprises an emulsifier.

In some embodiments, the composition further comprises a preservative.

In some embodiments, the pigment comprises an inorganic pigment. In some embodiments, the pigment comprises an organic pigment. In some embodiments, the pigment comprises a combination of organic pigment and inorganic pigment.

In some embodiments, the inorganic pigment is selected from the group consisting of: aluminum titanium dioxide, silicon dioxide, iron oxide, tin oxide, or any combination thereof.

In some embodiments, the acrylic polymer is selected from the group consisting of: ethylhexyl acrylate copolymer, dimethylaminoethyl methacrylate, methyl methacrylate, ethyl methacrylate, or any combination thereof.

In some embodiments, the composition comprises ethylhexyl acrylate copolymer, and dimethylaminoethyl methacrylate.

In some embodiments, the composition further comprises an ammonium acrylate.

In some embodiments, the ammonium acrylate is present at a concentration from 0.5% to 5%, by total weight of the composition.

In some embodiments, a total concentration of the ammonium acrylate, the ethylhexyl acrylate, and the dimethylaminoethyl methacrylate ranges from 20% to 45%, by total weight of the composition.

In some embodiments, the preservative is present at a concentration of 0.6% to 1.1%.

In some embodiments, the preservative comprises glycerin or a derivative thereof.

In some embodiments, the preservative comprises a material selected from the group consisting of: ethylhexylglycerin, propylene glycol, butylene glycol, caprylyl glycol, potassium sorbate, aromatic alcohol, chlorphenesin, or any combination thereof.

In some embodiments, the aromatic alcohol is phenoxyethanol.

In some embodiments, the fragrance is present at a concentration of from 5 to 35%, by weight.

In some embodiments, the fragrance is present at a concentration of from 10 to 30%, by total weight of the composition.

In some embodiments, the thickener is present at a concentration of from 0.1 to 2%, by total weight of the composition.

In some embodiments, the emulsifier is present at a concentration of from 0.1 to 6%, by total weight of the composition.

In some embodiments, the aqueous solution is present at a concentration of from 25 to 60%, by total weight of the composition.

In some embodiments, the pigment is present at a concentration of from 2 to 20%, by weight.

In some embodiments, the composition is a visible fragrance-releasing complex.

In some embodiments, a noticeable amount of fragrance is released for at least 15 hours.

In some embodiments, the fragrance comprises one or more materials selected from the group consisting of: an alcohol, an ether, a nitrile, an aldehyde, an ester, a ketone, a lactone, a thiol, an amine, a schiff-base, a terpene, a cyclic alkene, a cyclic oxide, an oxime, an essential oil, an aromatic species, or any combination thereof.

In some embodiments, the composition further comprises one or more non-aqueous solvents.

In some embodiments, the one or more non-aqueous solvents comprise glycerin.

In some embodiments, the one or more non-aqueous solvents are present at a concentration of 2% to 5%, by total weight of the composition.

In some embodiments, the composition further comprises a buffering agent.

In some embodiments, the buffering agent comprises a citrate.

In some embodiments, the composition is characterized by retaining a perceptible fragrance for at least seven days.

In some embodiments, the acrylic polymer has a viscosity of 50 to 200 mPas.

In some embodiments, the acrylic polymer has a density of 0.5 to 2 g/cm$^3$ at 20° C.

According to another aspect of the present invention, there is provided a method for conferring, enhancing, improving or modifying the odor properties of a body surface, comprising contacting or treating the body surface with the disclosed composition in an embodiment thereof.

In some embodiments, the method further comprises decorating the body surface.

According to another aspect of the present invention, there is provided a kit for applying a fragrance to a subject, comprising the disclosed composition in an embodiment thereof and means for topically applying the composition to a body surface of the subject.

In some embodiments, the applying the composition to the subject is further applying a body decoration.

DETAILED DESCRIPTION OF THE INVENTION

In one embodiment, the invention provides a composition and/or a fragrance-releasing complex comprising: at least one fragrance and a fragrance retention composition.

In one embodiment, the present invention provides a composition comprising: a fragrance; and a film-forming agent. In another embodiment, the film-forming agent comprises an acrylic polymer as described herein throughout.

In one embodiment, the disclosed composition comprises: a fragrance; an acrylic polymer, a thickener, and an aqueous solution In one embodiment, the present invention provides a composition comprising at least four components from (i) to (v): (i) an aqueous solution (ii) a fragrance; (iii) an acrylic polymer, (iv) a polymeric thickener, and (v) a pigment. In another embodiments, the composition comprises components (i) to (v). In another embodiment, the composition further comprises an emulsifier (also referred to as "component (vi)").

In another embodiment, the composition further comprises a non-aqueous solvent.

In another embodiment, the composition further comprises a non-aqueous solvent and an emulsifier.

In another embodiment, the composition further comprises a pigment.

In another embodiment, the composition further comprises a non-aqueous solvent and a pigment.

In another embodiment, the composition further comprises an emulsifier and a pigment. In another embodiment, the composition further comprises a non-aqueous solvent, an emulsifier and a pigment.

In another embodiment, "aqueous solution" refers to water. In another embodiment, an aqueous solution comprises water, distilled water, or purified water. In another embodiment, an aqueous solution comprises a buffer. In another embodiment, an aqueous solution is an isotonic buffer. Further embodiments of the buffer are described herein throughout. In another embodiment, an aqueous solution comprises 20% to 60% aqueous solution, by total weight of the composition. In another embodiment, an aqueous solution comprises 30% to 60% aqueous solution, by total weight of the composition. In another embodiment, an aqueous solution comprises 35% to 55% aqueous solution, by total weight of the composition. In another embodiment, an aqueous solution comprises 30%, 35%, 40%, 45%, 50%, 55%, or 60% aqueous solution, by total weight of the composition, including any value and range therebetween.

In another embodiment, an aqueous solution comprises 20% to 40%, or 20% to 30% aqueous solution, by total weight of the composition.

In another embodiment, the composition further comprises a pigment.

In another embodiment, the composition is a visible fragrance-releasing complex. In another embodiment, visible is visible light. In another embodiment, the phrase "visible light" refers to light having a wavelength of about 300 to 1000 nanometers (nm). In another embodiment, the phrase "visible light" refers to light having a wavelength of 300 nm, 400 nm, 500 nm, 600 nm, 700 nm, 800 nm, 900 nm, or 1000 nm, including any value and range therebetween.

In another embodiment, the composition as described herein comprises: aqueous solution, a fragrance; an acrylic polymer, a polymeric thickener, a pigment and a preservative. In another embodiment, the acrylic polymer is present at a concentration from 10% to 50%, or from 20% to 40%, by total weight of the composition. In another embodiment, the acrylic polymer is present at a concentration of 10%, 15%, 20%, 25%, 30%, 35%, 40%, 45%, or 50%, by total weight of the composition, including any value and range therebetween.

In exemplary embodiments, the acrylic polymer is present at a concentration of 20% to 40%, or 20% to 50%, by total weight.

In one embodiment, the composition is a fragrance-releasing complex (e.g., in the form of a formulation).

In one embodiment, the present invention provides a fragrance-releasing complex, wherein the weight ratio of the fragrance to the acrylic polymer is about 2:1 to 1:4, respectively. In another embodiment, the weight ratio of the fragrance to the acrylic polymer is about 1:4 to about 1:1, respectively. In another embodiment, the weight ratio of the fragrance to the acrylic polymer is about 1:4, respectively. In another embodiment, the weight ratio of the fragrance to the acrylic polymer is about 1:3, respectively. In another embodiment, the weight ratio of the fragrance to the acrylic polymer is about 1:2, respectively. In another embodiment, the weight ratio of the fragrance to the acrylic polymer is about 1:1, respectively. In another embodiment, the weight ratio of the fragrance to the acrylic polymer is about 1:4 to about 1:1, respectively.

In one embodiment, the present invention provides a fragrance-releasing complex, wherein the weight ratio of the fragrance to the acrylic polymer is at least 4:1. In another embodiment, the weight ratio of the fragrance to the acrylic polymer is at least 3:1. In another embodiment, the weight ratio of the fragrance to the acrylic polymer is at least 2:1. In another embodiment, the weight ratio of the fragrance to the acrylic polymer is at least 1:1. In another embodiment, the weight ratio of the fragrance to the acrylic polymer is at least 1:2. In another embodiment, the weight ratio of the fragrance to the acrylic polymer is at least 1:3.

In another embodiment, the weight ratio of the polymeric thickener to the acrylic polymer is from about 1:200 to 1:3, respectively. In another embodiment, the weight ratio of the polymeric thickener to the acrylic polymer is from about 1:150 to 1:3, respectively. In another embodiment, the weight ratio of the polymeric thickener to the acrylic polymer is from about 1:70 to 1:5, respectively. In another embodiment, the weight ratio of the polymeric thickener to the acrylic polymer is from about 1:30 to 1:5, respectively. In another embodiment, the weight ratio of the polymeric thickener to the acrylic polymer is from about 1:8 to 1:2, respectively. In another embodiment, the weight ratio of the polymeric thickener to the acrylic polymer is from 1:1 to 1:3, respectively. In another embodiment, the weight ratio of the polymeric thickener to the acrylic polymer is about 1:2, respectively.

In another embodiment, a composition of the invention is a scented body composition. In another embodiment, a composition of the invention is a topical scented body composition. In another embodiment, a composition of the invention is a topical scented colored body composition and/or decoration.

In another embodiment, the term "topical", as used herein, refers to a composition for application to the skin. In another embodiment, the term "topical" refers to a composition for application to the nail.

It is to be understood that the composition may applied on a variety of surfaces, without being limited to a skin surface.

In another embodiment, an emulsifier is a nonionic emulsifier. In another embodiment, an emulsifier is any nonionic emulsifier known to one of average skill in the art. In another embodiment, an emulsifier is a combination of emulsifiers e.g., a combination of nonionic emulsifiers. In another embodiment, an emulsifier is an ionic emulsifier.

In another embodiment, an emulsifier of the invention comprises from 20 to 30% solid content. In another embodiment, an emulsifier of the invention comprises from 22 to 28% solid content. In another embodiment, an emulsifier of the invention comprises about 25% solid content.

In another embodiment, an emulsifier has a viscosity of 150 to 300 mPas. In another embodiment, an acrylic polymer has a viscosity of 150 to 250 mPas. In another embodiment, an emulsifier has a viscosity of 180 to 220 mPas. In another embodiment, an emulsifier has a viscosity of about 200 mPas.

The terms "emulsifier" and "surfactant" are used herein-throughout interchangeably.

In another embodiment, an emulsifier is Glyceryl Stearate. In another embodiment, an emulsifier is a Polysorbate. In another embodiment, an emulsifier is Polysorbate 80. In another embodiment, an emulsifier is Polysorbate 20. In another embodiment, an emulsifier is Ceteareth-20. In another embodiment, an emulsifier comprises alkoxynated alcohol, e.g., ethoxylated alcohol.

In another embodiment, an emulsifier is ammonium acrylates copolymer comprising butylene glycol, acrylate copolymer, or a combination thereof.

Exemplary anionic surfactants include, but are not limited to, linear alkylbenzene sulfonates, alpha olefin sulfonates, paraffin sulfonates, alkyl ester sulfonates, alkyl sulfates, alkyl alkoxy sulfates, alkyl sulfonates, alkyl alkoxy carboxylates, alkyl alkoxylated sulfates, monoalkyl phosphates, dialkyl phosphates, sarcosinates, sulfosuccinates, isethionates, and taurates, as well as mixtures thereof. Further anionic surfactants that are suitable as the anionic surfactant component of the composition of the present invention include, without being limited thereto, ammonium lauryl sulfate, ammonium laureth sulfate, triethylamine lauryl sulfate, triethylamine laureth sulfate, triethanolamine lauryl sulfate, triethanol amine laureth sulfate, monoethanolamine lauryl sulfate, monoethanolamine laureth sulfate, diethanolamine lauryl sulfate, diethanol amine laureth sulfate, lauric monoglyceride sodium sulfate, sodium lauryl sulfate, sodium laureth sulfate, potassium lauryl sulfate, potassium laureth sulfate, sodium-monoalkyl phosphates, sodium dialkyl phosphates, sodium lauroyl sarcosinate, lauroyl sarcosine, cocoyl sarcosine, ammonium cocyl sulfate, ammonium lauryl sulfate, sodium cocyl sulfate, sodium trideceth sulfate, sodium tridecyl sulfate, ammonium trideceth sulfate, ammonium tridecyl sulfate, sodium cocoyl isethionate, disodium laureth sulfosuccinate, sodium dioctyl sulfosuccinate, sodium methyl oleoyl taurate, sodium laureth carboxylate, sodium trideceth carboxylate, sodium lauryl sulfate, potassium cocyl sulfate, potassium lauryl sulfate, monoethanolamine cocyl sulfate, sodium tridecyl benzene sulfonate, and sodium dodecyl benzene sulfonate.

In another embodiment, the emulsifier comprises disodium laureth sulfosuccinate, sodium lauryl sulfate, or a combination thereof.

In another embodiment, the composition as described herein comprises from 0.5 to 10% by weight emulsifier. In another embodiment, the composition as described herein comprises from 0.5 to 6% by weight emulsifier. In another embodiment, the composition as described herein comprises from 2 to 6% by weight emulsifier. In another embodiment, the composition as described herein comprises from 0.5 to 2.5% by weight emulsifier. In another embodiment the emulsifier presents in the composition at a concentration of 0.3% to 0.7%, by total weight of the composition. In another embodiment, the composition as described herein comprises from 0.5 to 1% by weight emulsifier.

In another embodiment, the emulsifier is present in the disclosed composition at a concentration of 0.1%, 0.2%, 0.3%, 0.4%, 0.5%, 0.6%, 0.7%, 0.8%, 0.9%, or 1%, by total weight of the composition, including any value and range therebetween.

In another embodiment, a composition of the invention comprises a fragrance-releasing complex. In another embodiment, the fragrance-releasing complex comprises a film forming agent.

In another embodiment, the term "film-forming agent" is meant to encompass compounds (or mixtures of compounds) which function to form a film onto the surface be treated (e.g., skin), thereby forming a barrier between the surface and the gaseous environment (e.g., air) above it.

In another embodiment, the film-forming agent forms a molecular or bi-molecular layer at the surface, thereby functioning as a substantially impermeable barrier, preventing transport of volatile species from a solid phase to the gaseous phase.

In another embodiment, the film-forming agent comprises an acrylic monomer or polymer. In another embodiment, the film-forming agent comprises an acrylic polymer as disclosed herein, e.g., at a concentration of 20 to 40%.

In exemplary embodiments, the film-forming agent is present at a concentration of 30%, by weight.

In another embodiment, the fragrance-releasing complex is adapted to extend fragrance retention within the fragrance-releasing complex.

In another embodiment, the term "acrylic polymer" refers to a polymer having at least 70 wt % polymerized residues of acrylic monomers, or, in another embodiment, at least 80 wt %, or, in another embodiment, at least 90 wt %, or, in another embodiment, at least 95 wt %, or, in another embodiment, at least 98 wt %, or, in another embodiment, at least 99 wt %.

In another embodiment, the term "acrylic monomers" refers to a monomer selected from, without being limited thereto, (meth) acrylic acids and/or their d-C22 alkyl, hydroxyalkyl or polyethylene glycol esters; crotonic acid, itaconic acid, fumaric acid, maleic acid, maleic anhydride, (meth)acrylamides, (meth)acrylonitrile and alkyl or hydroxyalkyl esters of crotonic acid, itaconic acid, fumaric acid, or maleic acid.

In another embodiment, the term "acrylic polymer" refers to a co-polymer. In another embodiment, the term "acrylic polymer" refers to an acrylic block copolymer.

In one embodiment, the term "block copolymer" refers to copolymers wherein monomeric units of a given type are organized in blocks, i.e. monomeric units of the same type are adjacent to each other. To explain further, the term "block copolymer" may include molecules of the type $A_iB_jA_k$, wherein A and B designate distinct types of monomers and the indices i, j, k and 1 are integer numbers having a value of at least 1.

In another embodiment, the term "acrylic co-polymer" refers to interpolymers of an acrylic monomer with one or more further acrylic monomers and/or with one or more nonacrylic monomer.

In another embodiment, the term "acrylic polymer" refers to a mixture of acrylates.

In another embodiment, the acrylic co-polymer is C3-20 alkyl acrylate copolymer. In another embodiment, the alkyl is substituted or, in another embodiment, the alkyl is non-substituted.

In another embodiment, the acrylic co-polymer is hexyl acrylate copolymer. In another embodiment, the acrylic co-polymer is ethylhexyl acrylate copolymer.

In another embodiment, the acrylic co-polymer is a methacrylate copolymer.

In another embodiment, the acrylic co-polymer is selected from, without being limited thereto, dimethylaminoethyl methacrylate, methyl methacrylate copolymer, ethyl methacrylate, or any combination thereof.

In another embodiment, the acrylic co-polymer comprises an acrylate copolymer having one or more ammonium groups (also referred to as: "ammonium acrylate copolymer").

In another embodiment, the composition comprises an acrylic polymer or a combination of acrylic polymers. In another embodiment, the acrylic polymer comprises starch or modified starch. In another embodiment, the acrylic polymer, is a: homopolymer, copolymer or multipolymer of one or more monomers including, but not limited to, acrylic acid, methacrylic acid, esters of acrylic acid and methacrylic acid (acrylates and methacrylates), acrylamides, acrylonitriles and derivatives, or any combinations thereof. In another embodiment, the acrylic polymer comprises acrylate monomers, such as but not limited to: Methacrylate, Methyl acrylate, Ethyl acrylate, 2-Chloroethyl vinyl ether, 2-Ethylhexyl acrylate, Hydroxyethyl methacrylate, Butyl acrylate, Butyl methacrylate, trimethylolpropane triacrylate (TMPTA) and any combination thereof. In another embodiment, the acrylic polymer is a copolymer-dispersion of acrylic and methacrylic acid esters.

In another embodiment, the fragrance retention composition comprises solid polymers such as PMMA (polymethyl methacrylate). In another embodiment, the fragrance retention composition comprises silica. In another embodiment, the fragrance retention composition comprises methyl methacrylate. In another embodiment, the fragrance retention composition comprises acrylated beads. In another embodiment, the fragrance retention composition comprises microparticles comprising polymers of the invention. In another embodiment, the fragrance retention composition comprises nanoparticles comprising polymers of the invention. In another embodiment, the acrylic polymer is a dispersion of acrylic and methacrylic acid esters.

In another embodiment, the composition of the present invention comprises acrylate and further comprises one or more compounds selected from: ethylhexyl acrylate copolymer, dimethylaminoethyl methacrylate, ammonium acrylate copolymer, and methacrylate copolymer.

In exemplary embodiments, the composition of the present invention comprises ethylhexyl acrylate copolymer, dimethylaminoethyl methacrylate, and ammonium acrylate copolymer.

In another embodiment, the one or more acrylic polymers are present in the composition at a concentration of 5% to 55%. In another embodiment, the one or more acrylic polymers are present in the composition at a concentration of 5% to 50%. In another embodiment, the one or more acrylic polymers are present in the composition at a concentration of 5% to 35%. In another embodiment, the one or more acrylic polymers are present in the composition at a concentration of 5% to 25%. In another embodiment, the one or more acrylic polymers are present in the composition at a concentration of 5% to 15%. In another embodiment the one or more acrylic polymers are present in the composition at a concentration of 7% to 12%.

In another embodiment, the one or more acrylic polymers are present in the composition at a concentration of: 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, or 60%, by total weight of the composition, including any value and range therebetween.

In another embodiment, the composition of the present invention comprises ethylhexyl acrylate copolymer. In another embodiment, the composition of the present invention comprises ethylhexyl acrylate copolymer at a concentration of 5% to 15%, by total weight of the composition. In another embodiment, the composition of the present invention comprises ethylhexyl acrylate copolymer at a concentration of 8% to 12%, by total weight of the composition. In another embodiment, the composition of the present invention comprises ethylhexyl acrylate copolymer at a concentration of concentration of 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, or 45%, by total weight of the composition, including any value and range therebetween. In another embodiment, the composition of the present invention comprises ethylhexyl acrylate copolymer at a concentration of about 5% to 15%, by total weight of the composition. In another embodiment, the composition of the present invention comprises ethylhexyl acrylate copolymer at a concentration of about 9%.

In another embodiment, the composition of the present invention comprises dimethylaminoethyl methacrylate. In another embodiment, the composition of the present invention comprises dimethylaminoethyl methacrylate at a concentration of 1% to 30%. In another embodiment, the composition of the present invention comprises dimethylaminoethyl methacrylate at a concentration of 1% to 20%. In another embodiment, the composition of the present invention comprises dimethylaminoethyl methacrylate at a concentration of 1% to 10%. In another embodiment, the composition of the present invention comprises dimethylaminoethyl methacrylate at a concentration of 1% to 3%, by total weight of the composition. In another embodiment, the composition of the present invention comprises dimethylaminoethyl methacrylate at a concentration of 1.5% to 3%, by total weight of the composition. In another embodiment, the composition of the present invention comprises dimethylaminoethyl methacrylate at a concentration of about 2.5%, by total weight of the composition.

In one embodiment, the acrylic polymer is within an emulsion. In another embodiment, an emulsion is oil in water emulsion. In another embodiment, an emulsion is water in oil emulsion. In another embodiment, the acrylic polymer is within dispersion. In another embodiment, the acrylic polymer is within a suspension.

In one embodiment, the emulsion comprises polyethyl acrylate, polymethyl acrylate, a copolymer of ethyl acrylate, and/or methyl methacrylate. In one embodiment, the emulsion comprises an ethylenically unsaturated compound such as, but not limited to: styrene. In another embodiment, the emulsion comprises a higher alkyl methacrylate.

In one embodiment, the emulsion is an acrylic paint. In one embodiment, the term "acrylic paint" refers to water based paint. In another embodiment, the term acrylic paint refers to latex paint. In another embodiment, the term acrylic paint refers to emulsion paint. In another embodiment, the term acrylic paint refers to water soluble paint.

In another embodiment, an acrylic polymer of the invention comprises from 30 to 50% solid content. In another embodiment, an acrylic polymer of the invention comprises from 35 to 45% solid content. In another embodiment, an acrylic polymer of the invention comprises about 40% solid content.

In another embodiment, an acrylic polymer has a viscosity of 50 to 200 mPas. In another embodiment, an acrylic polymer has a viscosity of 50 to 150 mPas. In another embodiment, an acrylic polymer has a viscosity of 80 to 120 mPas. In another embodiment, an acrylic polymer has a viscosity of about 100 mPas.

In another embodiment, an acrylic polymer of the invention has a density of 0.5 to 2.5 g/cm$^3$ at 20° C. In another embodiment, an acrylic polymer of the invention has a density of 0.7 to 2.2 g/cm$^3$ at 20° C. In another embodiment, an acrylic polymer of the invention has a density of 0.7 to 1.8 g/cm$^3$ at 20° C. In another embodiment, an acrylic polymer of the invention has a density of 0.8 to 1.5 g/cm$^3$ at 20° C.

In one embodiment, the composition comprises a fragrance.

In another embodiment, the composition comprises 1% to 40%, by weight, fragrance. In another embodiment, the composition comprises 5% to 30%, by weight, fragrance. In another embodiment, the composition comprises 10% to 25%, by weight, fragrance. In another embodiment, the composition comprises 15% to 25%, by weight, fragrance.

In one embodiment, this invention provides a composition comprising: a fragrance; and an acrylic polymer, wherein the fragrance is embedded within the acrylic polymer. In another embodiment, the fragrance-releasing complex is adapted to extend fragrance retention within the acrylic polymer. In another embodiment, the acrylic polymer retains a fragrance. In another embodiment, the acrylic polymer provides a solid or a semi-solid vehicle to a fragment. In another embodiment, the acrylic polymer provides a gel, a semi-gel, or a viscous vehicle to a fragment. In another embodiment, the acrylic polymer is in the form of a pattern that adheres to a body surface. In another embodiment, the fragrance-releasing complex is non-irritable, non-allergenic, non-toxic or any combination thereof to a body surface such as skin.

In one embodiment, the term "fragrance" means a compound of current use in perfumery, which is used essentially for its ability to smell pleasantly and to be capable of imparting a pleasant odor to the products into which it is incorporated, or to the surfaces, such as, but not limited to, skin or hair, to which it is applied, on its own or in admixture with other components.

In another embodiment, a fragrance is a composition capable to impart or modify the odor of a surface such as a body surface.

In another embodiment, a fragrance is a composition that has the ability to mask a malodor of a surface.

In one embodiment, the fragrance comprises an alcohol such as ethanol. In another embodiment the fragrance comprises a perfume concentrate. In another embodiment, the fragrance comprises an eaux de parfum. In another embodiment, the fragrance comprises an eaux de toilette. In another embodiment, the fragrance comprises a cologne. In another embodiment, the fragrance comprises a body splash.

In one embodiment, a volatile fragrance has a boiling point of less than about 475° C. to 525° C. In another embodiment, a volatile fragrance has a boiling point of less than about 475° C. to 515° C. In another embodiment, a volatile fragrance has a boiling point of less than about 485° C. to 515° C. In another embodiment, a volatile fragrance has a boiling point of less than about 495° C. to 505° C. In another embodiment, a volatile fragrance has a boiling point of less than about 500° C.

In one embodiment, a volatile fragrance is a highly volatile fragrance. In one embodiment, highly volatile fragrance means having a boiling point of about 230° C. to 250° C. or lower. In another embodiment highly volatile fragrance means having a boiling point of about 230° C. to 245° C. or lower. In another embodiment highly volatile fragrance means having a boiling point of about 235° C. to 245° C. or lower. In another embodiment highly volatile fragrance means having a boiling point of about 250° C. or lower.

In another embodiment, the highly volatile fragrance comprises a component selected from, without being limited thereto: anethole, benzaldehyde, benzyl acetate, benzyl alcohol, benzyl formate, iso-bornyl acetate, camphene, cis-citral (neral), citronellal, citronellol, citronellyl acetate, para-cymene, decanal, dihydrolinalool, dihydromyrcenol, dimethyl phenyl carbinol, eucalyptol. geranial, geraniol, geranyl acetate, geranyl nitrile, cis-3-hexenyl acetate, hydroxycitronellal, d-limonene, linalool, linalool oxide, linalyl acetate, linalyl propionate, methyl anthranilate, alpha-methyl (or isomethyl) ionone, methyl nonyl acetaldehyde, methyl phenyl carbinyl acetate, laevo-menthyl acetate, menthone, isomenthone, myrcene, myrcenyl acetate, myrcenol, nerol, neryl acetate, nonyl acetate, phenyl ethyl alcohol, alpha-pinene, beta-pinene, gamma-terpinene, alpha-terpineol, beta-terpineol, terpinyl acetate, and vertenex (para-tertiary-butyl cyclohexyl acetate), and any combination thereof.

In one embodiment, a volatile fragrance is a moderately volatile fragrance. In one embodiment, a moderately volatile fragrance means having a boiling point of about 250° C. to 300° C. In another embodiment a moderately volatile fragrance means having a boiling point of about 250° C. to 300° C. In another embodiment a moderately volatile fragrance means having a boiling point of about 250° C. to 290° C. In another embodiment a moderately volatile fragrance means having a boiling point of about 260° C. to 290° C. In another embodiment a moderately volatile fragrance means having a boiling point of about 260° C. to 280° C.

In another embodiment, the moderately volatile fragrance comprises a component selected from, without being limited thereto: amyl cinnamic aldehyde, iso-amyl salicylate, beta-caryophyllene, cedrene, cinnamic alcohol, coumarin, dimethyl benzyl carbinyl acetate, ethyl vanillin, eugenol, iso-eugenol, for acetate, heliotropine, 3-cis-hexenyl salicylate, hexyl salicylate, lilial (para-tertiarybutyl-alpha-methyl hydrocinnamic aldehyde), gamma-methyl ionone, nerolidol, patchouli alcohol, phenyl hexanol, beta-selinene, trichloromethyl phenyl carbinyl acetate, triethyl citrate, vanillin, veratraldehyde and any combination thereof.

In one embodiment, a volatile fragrance is a less volatile fragrance. In one embodiment, a less volatile fragrance means having a boiling point of about 300° C. to 500° C. In another embodiment a less volatile fragrance means having a boiling point of about 300° C. to 450° C. In another embodiment a less volatile fragrance means having a boiling point of about 350° C. to 450° C.

In another embodiment, the less volatile fragrance comprises a component selected from the without being limited thereto: benzophenone, benzyl salicylate, ethylene brassyiate, galaxolide (1,3,4,6,7,8-hexahydro-4,6,6,7,8,8-hexamethyl-cyclopenta-gama-2-benzopyran), hexyl cinnamic aldehyde, lyral (4-(4-hydroxy-4-methyl pentyl)-3-cyclohexene-10-carboxaldehyde), methyl cedrylone, methyl dihydro jasmonate, methyl-beta-naphthyl ketone, musk indanone, musk ketone, musk tibetene, phenylethyl phenyl acetate, and any combination thereof.

In another embodiment, a composition of the invention comprises a buffering agent. In another embodiment, the buffering agent comprises a citrate buffer. In another embodiment, the citrate buffer is sodium citrate. In another embodiment, the buffering agent has a sufficient buffering capacity to control the acidity (pH value) of the composition.

In another embodiment, a composition of the invention has a pH value of 6 to 9. In another embodiment, a composition of the invention has a pH value of 7 to 9. In another embodiment, a composition of the invention has a pH value of 7.5 to 8.5.

In another embodiment, a composition of the invention comprises a buffering agent (e.g., sodium citrate) at a concentration of 0.005% to 0.05%, by total weight of the composition. In another embodiment, the composition of the invention comprises a buffering agent at a concentration of 0.008% to 0.02%, by total weight of the composition.

In another embodiment, a composition of the invention comprises a buffering agent (e.g., sodium citrate) at a concentration of 0.005%, 0.006%, 0.007%, 0.008%, 0.009%, 0.01%, 0.012%, 0.014%, 0.016%, 0.018%, or 0.02%, by total weight of the composition, including any value and range therebetween.

In another embodiment, a composition of the invention comprises one or more non-aqueous solvents. In another embodiments, the one or more non-aqueous solvents comprise polyol. In another embodiment, the polyol is glycerin.

In another embodiment, the one or more non-aqueous solvents are present at a concentration of 0.5% to 6%. In another embodiment, the one or more non-aqueous solvents are present at a concentration of 2% to 5%. In another embodiment, the one or more non-aqueous solvents are present at a concentration of 0.5%, 1%, 2%, 3%, 4%, 5%, or 6%, including any value and range therebetween.

In another embodiment, a composition of the invention comprises one or more preservatives.

In another embodiment, the one or more preservatives are present at a concentration of 0.1% to 7%, by total weight of the composition. In another embodiment, the one or more preservatives are present at a concentration of 0.05% to 3%, or 0.5 to 2%, by total weight of the composition. In another embodiment, the one or more preservatives are present at a concentration of 0.05%, 0.1%, 0.2%, 0.3%, 0.4%, 0.5%, 0.6%, 0.7%, 0.8%, 0.9%, 1%, 1.1%, 1.2%, 1.3%, 1.4%, 1.5%, 2%, 2.5%, 3%, 3.5%, 4%, 4.5%, 5%, 5.5%, 6%, 6.5%, or 7%, by total weight of the composition, including any value and range therebetween.

In another embodiments, the one or more preservatives comprise glycerin derivative. In another embodiments, the one or more preservatives comprise ethylhexylglycerin. In another embodiments, the one or more preservatives comprise aromatic alcohol. In another embodiments, the one or more preservatives comprise chlorphenesin. In another embodiments, the aromatic alcohol is phenoxyethanol.

In another embodiments, the one or more preservatives are selected from, without being limited thereto, glycerin, phenoxyethanol, caprylyl glycol, butylene glycol, potassium sorbate, ethylhexylglycerin, or any combination thereof.

In another embodiments, the one or more preservatives comprise phenoxyethanol, and propane-diol or a derivative thereof, e.g., ethylhexylglycerin.

In another embodiments, the one or more preservatives comprise glycol or a derivative thereof, for example and without being limited thereto, propylene glycol, butylene glycol, and caprylyl glycol, or any combination thereof.

In another embodiment, the composition of the invention comprises one or more thickeners (also referred to as: "viscosity controlling agents").

In another embodiment, a thickener is a cosmetic thickener. In another embodiment, a thickener comprises cellulose or a derivative thereof. In another embodiment, a thickener is an aqueous thickener. In another embodiment, a thickener comprises a gum. In another embodiment, a thickener comprises a carbomer. In another embodiment, a thickener comprises a polyethylene glycol. In another embodiment, a thickener comprises a non-aqueous thickener. In another embodiment, a thickener is an organic thickener.

In another embodiment, a thickener is polysaccharide. In another embodiment, a thickener is a gum. In another embodiment, a thickener is xanthan gum. In another embodiment, a thickener is xanthan a gum. In another embodiment, a thickener is gellan gum. In another embodiment, a thickener is welan gum. In another embodiment, a thickener is guar gum. In another embodiment, a thickener is a carob flour.

In another embodiment, a thickener has a density of at least 1 g/cm$^3$. In another embodiment, a thickener has a density of 1 to 2.5 g/cm$^3$. In another embodiment, a thickener has a density of 1.2 to 2.0 g/cm$^3$. In another embodiment, a thickener has a density of 1 to 1.8 g/cm$^3$. In another embodiment, a thickener has a density of 1.4 to 2.0 g/cm$^3$. In another embodiment, a thickener has a density of about 1.6 g/cm$^3$.

In another embodiment, a thickener of the invention has a density of 0.5 to 2.5 g/cm$^3$ at 20° C. In another embodiment, a thickener of the invention has a density of 0.7 to 2.2 g/cm$^3$ at 20° C. In another embodiment, a thickener of the invention has a density of 0.7 to 1.8 g/cm$^3$ at 20° C. In another embodiment, a thickener of the invention has a density of 0.9 to 1.6 g/cm$^3$ at 20° C.

In another embodiment, a thickener is characterized by a rheological property e.g., viscosity. In another embodiment, a thickener has a viscosity (at 1% solution of the thickener in aqueous solution, by weight) of 1000 to 2000 cps, or 1100 to 2000 cps. In another embodiment, a thickener has a viscosity of 1200 to 2000 cps. In another embodiment, a thickener has a viscosity of 1300 to 2000 cps. In another embodiment, a thickener has a viscosity of 1300 to 1900 cps. In another embodiment, a thickener has a viscosity of 1300 to 1800 cps.

In another embodiment, a thickener is present at a concentration of: 0.1%, 0.5%, 1%, 2%, 3%, 4%, or 5%, by total weight of the composition, including any value and range therebetween. In another embodiment, a thickener is present at a concentration of 0.1 to 2%, by weight.

In one embodiment, the fragrance retention composition comprises a pigment.

In another embodiment, the composition as described herein comprises from 1 to 20% by weight pigment.

In another embodiment, the terms "pigment", and "cosmetic colorant" are used interchangeably.

In another embodiment, the pigment imparts color and/or other opacity and/or other visual effect to the composition. In another embodiment, the term "opacity" indicates that the transparency of an object changes such that the object becomes gradually vivid, dim, or the like.

In another embodiment, the composition as described herein comprises from 2 to 20% by weight pigment. In another embodiment, the composition as described herein comprises from 5 to 10% by weight pigment. In another embodiment, the composition as described herein comprises from 3 to 7% by weight pigment. In another embodiment, the composition as described herein comprises 1%, 2%, 3%, 4%, 5%, 6%, 7%, 8%, 9%, 10%, 11%, 12%, 13%, 14%, 15%, 16%, 17%, 18%, 19%, or 20% pigment, by total weight, including any value and range therebetween.

In one embodiment, the pigment is an organic pigment. In another embodiment, the pigment is an inorganic pigment. In another embodiment, the pigment is in the form of a coating layer. In another embodiment, the pigment is pretreated prior to its incorporation in the disclosed composition. In another embodiment, the pigment is a combination of pigments. In one embodiment, the pigment is a combination of inorganic and organic pigments. In another embodiment, the pigment is a colorant. In another embodiment, the pigment comprises a combination of colorants. In another embodiment, the pigment is a dye. In another embodiment, the pigment comprises a combination of dyes. In one embodiment, the pigment comprises a colored component. In another embodiment, the pigment comprises a combination of colored components. In another embodiment, the pigment is an ink. In another embodiment, the pigment comprises a combination of inks.

In another embodiment, the pigment comprises: an anthraquinone, a phthalocyanine, a pyrroline, a triphenodioxazine, a methine, a benzodifuranone, a coumarin, an indoaniline, a benzenoid, a xanthene, a phenazine, a solvent soluble sulphur dye, a quinophthalone, a pyridone, an aminopyrazoie, a pyrollidine, a styrylic, or any combination thereof. In another embodiment, the pigment comprises an azoic, such as, but not limited to, a monoazo, a disazo, a trisazo, or any combination thereof. In another embodiment, the pigment comprises an azoic containing a heterocyclic group.

In another embodiment, an inorganic pigment of the invention comprises a mineral.

In another embodiment, an inorganic pigment of the invention comprises aluminum. In another embodiment, a pigment of the invention comprises titanium dioxide (e.g., CI 77891). In another embodiment, a pigment of the invention comprises silicon dioxide. In another embodiment, a pigment of the invention comprises iron oxide (e.g., CI 77499). In another embodiment, a pigment of the invention comprises tin oxide. In another embodiment, a pigment of the invention comprises mica.

In one embodiment, the fragrance-releasing complex comprises a retention composition. In another embodiment, the fragrance-releasing complex comprises a combination of retention compositions. In one embodiment, the fragrance-releasing complex comprises a fragrance. In another embodiment, the fragrance-releasing complex comprises a combination of fragrances. In another embodiment, the present invention provides a composition and/or a fragrance-releasing complex comprising one or more fragrances and one or more fragrance retention compositions. In another embodiment, the fragrance-releasing complex comprises an admixture or an accord. In another embodiment, the fragrance retention composition comprises a dispersing agent.

In another embodiment, the fragrance retention composition comprises a solubilization accelerating agent. In another embodiment, the fragrance retention composition comprises an inorganic filler. In another embodiment, the fragrance retention composition comprises a binding agent. In another embodiment, the fragrance retention composition comprises a resin. In another embodiment, the fragrance retention composition comprises a rheological agent. In another embodiment, the fragrance retention composition comprises an anti-foaming agent. In another embodiment, the fragrance retention composition comprises stabilizer. In another embodiment, the stabilizer allows to increase viscosity, or reduce shear forces.

In another embodiment, the stabilizer is dispersing agent. In another embodiment, the stabilizer is a thermal stabilizer.

Exemplary Compositions

In one embodiment, a composition as described herein comprises at least three, a least four or at least five or all components (i) to (v) (the percent is expressed by total weight of the composition): (i) aqueous solution (20 to 65%); (ii) fragrance (10 to 30%); (iii) acrylate or a copolymer thereof (20 to 40%); (iv) a pigment, e.g., titania (2 to 10%), (v) a thickener e.g., xanthan gum (0.5 to 1.5%), and one or more emulsifiers (2-6%).

In exemplary embodiments the emulsifier is selected from, without being limited thereto, polyethylene glycol ether, sodium laureth sulfate, caprylyl glycol, carboxylic acid (C11-15 Pareth-7), sodium citrate, butylene glycol, ethylhexylglycerin, potassium sorbate, sodium lauryl sulfate disodium, and laureth sulfosuccinate. In another embodiment, the composition comprises ammonium acrylate copolymer (0.5 to 2% or 0.5 to 3%).

In another embodiment, a composition as described herein comprises (the percent is expressed by total weight of the composition): aqueous solution (20 to 60%), fragrance (10 to 25%), acrylate or a copolymer thereof (25 to 35%), and one or more from (5 to 10%): a pigment (e.g., iron oxide), glycerin, xanthan gum, or citrate, and one or more from (0.3 to 1%): ethylhexylglycerin and phenoxyethanol.

In another embodiment, the composition further comprises ammonium acrylate copolymer (0.5 to 2%, 0.5 to 3%, or 2% to 5%).

Properties of the Compositions

In one embodiment, a composition as described herein is stable after being applied to a surface, such as a skin or a body surface and is dried. In another embodiment, a stable composition is a composition not been affected by cracks and/or peelings. In another embodiment, a stable composition is a composition which releases noticeable amount of fragrance for at least 8 hours. In another embodiment, a stable composition is a composition which releases a noticeable amount of fragrance for at least 10 hours. In another embodiment, a stable composition is a composition which releases a noticeable amount of fragrance for at least 12 hours. In another embodiment, a stable composition is a composition which releases a noticeable amount of fragrance for at least 15 hours. In another embodiment, a stable composition is a composition which releases a noticeable amount of fragrance for at least 20 hours. In another embodiment, a stable composition is a composition which releases a noticeable amount of fragrance for at least 24 hours. In another embodiment, a stable composition is a composition which releases a noticeable amount of fragrance for 8 to 36 hours.

In another embodiment, a stable composition is a composition which releases a noticeable amount of fragrance within 0.1 to 120 seconds from applying it to a skin surface (immediate fragrance release). In another embodiment, a stable composition is a composition which releases a noticeable amount of fragrance within 1 to 15 seconds from applying it to a skin surface (immediate fragrance release). In another embodiment, a stable composition is a composition which releases a noticeable amount of fragrance within 5 to 30 seconds from applying it to a skin surface (immediate fragrance release). In another embodiment, a stable composition is a composition which releases a noticeable amount of fragrance within 10 to 40 seconds from applying it to a skin surface (immediate fragrance release).

In one embodiment, the term "comprises" includes or can be replaced with the term "consists".

In one embodiment, the term "about", as used herein, means within 10% of the recited numerical value; In another embodiment, the term "about" as used herein, means within 5% of the recited numerical value.

In one embodiment, the term "fragrance-releasing complex" is synonymous with the term "composition" as used herein.

In another embodiment, a composition comprising: a fragrance; an acrylic polymer, a thickener, an emulsifier, an aqueous solution, and a pigment is used for skin or a body surface decoration. In another embodiment, a composition as described herein is active for at least 10 hours. In another embodiment, a composition as described herein is active for at least 12 hours. In another embodiment, a composition as described herein is active for at least 15 hours. In another embodiment, a composition as described herein is active for at least 18 hours. In another embodiment, a composition as described herein is active for at least 20 hours. In another embodiment, a composition as described herein is active for 10 to 40 hours. In another embodiment, a composition as described herein is active for 10 to 48 hours. In another embodiment, a composition as described herein is active for 10 to 30 hours. In another embodiment, a composition as described herein is active for 10 to 25 hours.

In another embodiment, the term "active" refers to being visible upon placement on a surface such as a body surface. In another embodiment, a composition as described herein is active upon exposure to air. In another embodiment, a composition as described herein is active upon exposure to air but not to liquid. In another embodiment, the term "active" refers to providing a noticeable amount of fragrance for at least 5 hours. In another embodiment, the term "active" refers to providing a noticeable amount of fragrance for at least 10 hours. In another embodiment, the term "active" refers to providing a noticeable amount of fragrance for at least 15 hours. In another embodiment, the term "active" refers to providing a noticeable amount of fragrance for at least 25 hours. In another embodiment, the term "active" refers to providing a noticeable amount of fragrance for 5 to 40 hours. In another embodiment, the term "active" refers to providing a noticeable amount of fragrance for 10 to 40 hours. In another embodiment, the term "active" refers to providing a noticeable amount of fragrance for 15 to 40 hours. In another embodiment, the term "active" refers to providing a noticeable amount of fragrance for 15 to 35 hours.

In another embodiment, by "noticeable scent or fragrance" it is meant to at least one healthy adult individual being able to detect or smell a fragrance from a composition placed at a distance of 5 cm from his or hers nose. In another embodiment, "noticeable" is smellable (capable of being smelled) amount of fragrance noticed by healthy and normal human nose of three adult female individuals from a distance of 5 cm from the composition as described herein. In another embodiment, by "unnoticeable scent or fragrance" it is meant to refer to least one healthy adult female individual out of three adult female individuals not being able to detect or smell a fragrance from a composition placed at a distance of 5 cm from her nose.

In another embodiment, the composition as described herein solidifies, dries, and/or stabilizes within 5 to 50 seconds after exposure to air at a temperature of 15 to 30° C. In another embodiment, the composition as described herein solidifies, dries, and/or stabilizes within 5 to 50 seconds after it is applied on a body surface at an ambient temperature of 15 to 30° C. In another embodiment, the composition as described herein solidifies, dries, and/or stabilizes within 5 to 50 seconds after it is applied onto the skin at an ambient temperature of 15 to 30° C. In another embodiment, the composition as described herein solidifies, dries, and/or stabilizes within 5 to 50 seconds after it is applied onto a cloth at an ambient temperature of 15 to 30° C. In another embodiment, a stabilized composition is a composition that does not stain another surface upon contact with another surface. In another embodiment, a stabilized composition is a solid composition. In another embodiment, a stabilized composition is a composition that sticks to a body surface.

In another embodiment, the composition as described herein solidifies, dries, and/or stabilizes within 5 to 30 seconds. In another embodiment, the composition as described herein solidifies, dries, and/or stabilizes within 10 to 40 seconds. In another embodiment, the composition as described herein solidifies, dries, and/or stabilizes within 10 to 20 seconds. In another embodiment, the composition as described herein solidifies, dries, and/or stabilizes within 10 to 30 seconds.

In another embodiment, a composition as described herein is capable of drying within a short period of time, after being applied to the skin or a body surface. In another embodiment, by a "short period of time" it is meant within 1 sec, 2 sec, 3 sec, 4 sec, 5 sec, 6 sec, 7 sec, 8 sec, 9 sec, 10 sec, 11 sec, 12 sec, 13 sec, 14 sec, 15 sec, 16 sec, 17 sec, 18 sec, 19 sec, or 20 sec, including any value and range therebetween.

In another embodiment, each physical measure described herein is obtained under standard conditions for temperature and pressure (STP) or STAP if not otherwise stated.

In one embodiment, the fragrance retention composition has the capacity to affect the characteristics of the fragrance composition, such as but not limited to, limiting evaporation rate and intensity, in a manner that can be perceived by an observer or user thereof, over time, as compared to the same perception in the absence of the fragrance retention composition. In another embodiment, the fragrance retention composition is non-irritable, non-allergenic, non-toxic or any combination thereof to a body surface such as skin. In another embodiment, the fragrance retention composition thickens upon exposure to air. In another embodiment, the fragrance retention composition dries upon exposure to air. In another embodiment, the fragrance retention composition solidifies upon exposure to air.

In another embodiment, the composition as described herein is characterized by smoothness after it is applied on a body surface at an ambient temperature of 15 to 30° C.

In another embodiment, the composition as described herein is characterized as being non-grainy after it is applied on a body surface at an ambient temperature of 15 to 30° C.

In another embodiment, the composition retains a perceptible fragrance.

In another embodiment, "retains a perceptible fragrance" is retains a perceptible fragrance after applied to a body surface. In another embodiment, "retains a perceptible fragrance" is smellable or detected by smell from a distance of 5 cm as described herein. In one embodiment, the fragrance-releasing complex retains a perceptible fragrance for at least 7 days. In another embodiment, the fragrance-releasing complex retains a perceptible fragrance attributable to the composition and/or the fragrance-releasing complex for 24 hours to 18 days. In another embodiment, the composition and/or the fragrance-releasing complex retains a perceptible fragrance attributable to the composition and/or the fragrance-releasing complex for 24 hours to 16 days. In another embodiment, the composition and/or the fragrance-releasing complex retains a perceptible fragrance attributable to the composition and/or the fragrance-releasing complex for 3 to 16 days. In another embodiment, the composition and/or the fragrance-releasing complex retains a perceptible fragrance attributable to the composition and/or the fragrance-releasing complex for 3 to 14 days. In another embodiment, the composition and/or the fragrance-releasing complex retains a perceptible fragrance attributable to the composition and/or the fragrance-releasing complex for 5 to 14 days. In another embodiment, the composition and/or the fragrance-releasing complex retains a perceptible fragrance attributable to the composition and/or the fragrance-releasing complex for 5 to 12 days. In another embodiment, the composition and/or the fragrance-releasing complex retains a perceptible fragrance attributable to the composition and/or the fragrance-releasing complex for 7 to 10 days. In another embodiment, the composition and/or the fragrance-releasing complex retains a perceptible fragrance attributable to the composition and/or the fragrance-releasing complex for 7 days. In another embodiment, the composition and/or the fragrance-releasing complex retains a perceptible fragrance attributable to the composition and/or the fragrance-releasing complex for 10 days.

In another embodiment, the composition and/or the fragrance-releasing complex retains a perceptible fragrance attributable to the composition and/or the fragrance-releasing complex for 10 to 50 hours. In another embodiment, the composition and/or the fragrance-releasing complex retains a perceptible fragrance attributable to the composition and/or the fragrance-releasing complex for 10 to 40 hours. In another embodiment, the composition and/or the fragrance-releasing complex retains a perceptible fragrance attributable to the composition and/or the fragrance-releasing complex for 15 to 50 hours. In another embodiment, the composition and/or the fragrance-releasing complex retains a perceptible fragrance attributable to the composition and/or the fragrance-releasing complex for 10 to 30 hours. In another embodiment, the composition and/or the fragrance-releasing complex retains a perceptible fragrance attributable to the composition and/or the fragrance-releasing complex for 15 to 30 hours. In another embodiment, the composition and/or the fragrance-releasing complex retains a perceptible fragrance attributable to the composition and/or the fragrance-releasing complex for 18 to 28 hours. In another embodiment, the composition and/or the fragrance-releasing complex retains a perceptible fragrance attributable to the composition and/or the fragrance-releasing complex for 20 to 30 hours.

In another embodiment, a composition as described herein is characterized by a non-sticky feeling. In another embodiment, a composition as described herein is characterized by a smooth feeling. The term "sticky feeling" is used herein to indicate a property of a cosmetic or dermatological composition which gives sticky or tacky feeling to the body surface (e.g., skin and/or nail), when the composition is applied on a body surface.

In another embodiment, a composition as described herein is characterized by a desired durability. In another embodiment, by "desired durability" it is meant that upon applying on a body surface, the composition exhibits minimal loss of definition for at least 10 hours, at least 15, hours at least 20 hours, at least 25 hours, at least 30 hours, at least 35 hours, at least 40 hours, or for at least 45 hours, post application.

In another embodiment, "minimal loss of definition" means that at least 20%, at least 30%, at least 40%, at least 50%, at least 60%, at least 70%, or at least 80%, by weight, of the composition remains adhered to the body surface In another embodiment, a composition as described herein is characterized by pH above 6.5. In another embodiment, a composition as described herein is characterized by pH 7, 7.5, 8, 8.5, 9, or 9.5, including any value and range therebetween.

Antimicrobial Properties

In another embodiment, a composition as described herein is characterized by an antimicrobial property.

In another embodiment, "antimicrobial activity" is referred to as an ability to inhibit (prevent), reduce or retard bacterial growth, fungal growth, biofilm formation or eradicate living bacterial cells, or their spores, yeast, or fungal cells or viruses in a suspension or in a moist environment.

Herein, inhibiting or reducing or retarding the formation of load of a microorganism refers to inhibiting reducing or retarding growth of microorganisms and/or eradicating a portion or all of an existing population of microorganisms.

The microorganism can be, for example, a unicellular microorganism (prokaryotes, archaea, bacteria, eukaryotes, protists, fungi (e.g., *Candida albicans*), algae, euglena, protozoan, dinoflagellates, apicomplexa, trypanosomes, amoebae and the likes), or a multicellular microorganism.

In another embodiment, the microorganism comprises bacterial cells of bacteria such as, for example, Gram-positive and Gram-negative bacteria. Exemplary bacteria are selected from without being limited thereto, *S. aureus*, and *Pseudomonas aeruginosa*.

In another embodiment, the term "preventing" indicates that the growth rate of the microorganism cells is essentially nullified or is reduced by at least 20%, at least 30%, at least 40%, at least 50%, at least 60%, at least 70%, at least 80%, at least 90%, at least 99% or at least 99.9%, including any value therebetween, of the appearance of the microorganism in a comparable situation lacking the presence of a composition of the invention.

Methods for determining a level of appearance of a microorganism cells are known in the art.

Methods for Modifying the Odor Properties

In one embodiment, the present invention provides a method for conferring, enhancing, improving or modifying the odor properties of a body surface, contacting or treating the body surface with the composition and/or the fragrance-releasing complex as described herein.

In one embodiment, the present invention provides a method for decorating a body surface. In another embodiment, the body surface is skin. In one embodiment, the present invention provides a kit for applying a fragrance to a subject, comprising a fragrance-releasing complex; and means for topically applying the composition and/or the fragrance-releasing complex to a body surface of a subject.

In one embodiment, the kit comprises a stencil having a decorative shape therein. In another embodiment, the kit comprises a transferable sheet with a decorative shape thereon. In another embodiment, the kit comprises a cutout in the shape of the body decoration. In another embodiment, the kit comprises an image or pattern to be placed on any part of the human body.

In another embodiment, the kit comprises decorative element comprising a substrate, a decorative pattern thereon. In another embodiment, the substrate comprises a plastic film. In another embodiment, the plastic film comprises a polymer selected from the following: polyethylene, polypropylene, polyester, polyvinyl chloride and plasticized polyvinyl chloride; a metalized plastic film; and a metal foil.

In another embodiment, the plastic film has a thickness of about 0.01 mm to 0.5 mm. In another embodiment, the plastic film has a thickness of about 0.01 mm to 0.45 mm. In another embodiment, the plastic film has a thickness of about 0.05 mm to 0.45 mm. In another embodiment, the plastic film has a thickness of about 0.05 mm to 0.4 mm. In another embodiment, the plastic film has a thickness of about 0.1 mm to 0.4 mm. In another embodiment, the plastic film has a thickness of about 0.1 mm to 0.35 mm. In another embodiment, the plastic film has a thickness of about 0.15 mm to 0.35 mm. In another embodiment, the plastic film has a thickness of about 0.15 mm to 0.3 mm. In another embodiment, the plastic film has a thickness of about 0.2 mm to 0.25 mm.

In another embodiment, the kit comprises an adhesive sheet. In another embodiment, the adhesive sheet comprises an adhesive component selected from, without being limited thereto, acrylic emulsion, a solvent-based acrylic and an acrylic hot melt adhesive.

In another embodiment, the kit comprises a decorative template that covers one or more regions of the body area. In another embodiment, the decorative template limits application of the composition and/or the fragrance-releasing complex to those regions of the body area not covered by the decorative template. In another embodiment, the body area is selected from the group comprising skin, nails, teeth, and any combination thereof. In another embodiment, the kit is for home use. In one embodiment, the present invention provides a kit for decorating a body surface with a composition or a complex as described herein. In one embodiment, the present invention provides a kit wherein the composition and/or the fragrance-releasing complex further comprise a pigment.

EXAMPLES

Reference is now made to the following examples, which together with the above descriptions illustrate some embodiments of the invention in a non-limiting fashion.

Different formulae of the invention were applied to the skin around the arm of an adult user. The specific water based components were selected as they provide short drying/stabilization period and sufficient elasticity. Likewise, a thickener was chosen as it stabilized the emulsion, optimized it rheological behavior, its homogeneity, enhanced drying increased elasticity. Exemplary 6 formulae are presented herein (see Tables 1-6 below) and were evaluated according to the hereinbelow procedures.

Exemplary Compositions

TABLE 1

Formula no. 1

| INCI | % |
| --- | --- |
| Fragrance | 15-30 |
| Ethanol | 25-60 |
| Mica and Titanium Dioxide and Iron Oxides | 8 |
| Polyimide-1 and Aqua | 10 |
| Fumed silica and HMDS* | 6 |
| Octylacrylamide and Acrylates and Butylaminoethyl Methacrylate Copolymer | 5 |
| Total | 100 |

*hexamethyldisilazane

TABLE 2

Formula no. 2

| INCI | % |
| --- | --- |
| Fragrance | 15-30 |
| Ethanol | 15-30 |
| Mica and Titanium Dioxide and Iron Oxides | 10 |
| Acrylates Copolymer | 0.2 |
| Aqua | 25-60 |
| Polyquaternium-4 | 2 |
| Octylacrylamide and Acrylates and Butylaminoethyl Methacrylate Copolymer | 3 |
| Triethanolamine | 0.1 |
| Total: | 100 |

TABLE 3

Formula no. 3

| INCI | % |
| --- | --- |
| Fragrance | 15-30 |
| Ethanol | 25-60 |
| Synthetic Fluorphlogopite and Iron Oxide | 8 |
| Mica and Titanium Dioxide and Iron Oxides | 2 |
| polyacrylate crosspolymer-6 | 2 |
| Aqua | 14.9 |
| Polyquaternium-4 | 5 |
| Octylacrylamide and Acrylates and Butylaminoethyl Methacrylate Copolymer | 5 |
| Triethanolamine | 0.1 |
| Total | 100 |

TABLE 4

Formula no. 4

| INCI | % |
| --- | --- |
| Fragrance | 15-30 |
| Ethanol | 25-60 |
| Mica and Titanium Dioxide and Iron Oxides | 8 |
| Polyimide-1 and Aqua | 9 |
| Silica | 4 |
| Octylacrylamide and Acrylates and Butylaminoethyl Methacrylate Copolymer | 5 |
| Total | 100 |

TABLE 5

Formula no. 5

| INCI | % |
| --- | --- |
| Polyimide-1 and Aqua | 27 |
| Fragrance | 15-30 |
| Ethanol | 25-60 |
| Synthetic Fluorphlogopite and Iron Oxide | 8 |
| Mica and Titanium Dioxide and Iron Oxides | 2 |
| Total | 100 |

TABLE 6

Formula no. 6 (Exemplary approved formula)

| INCI | % |
| --- | --- |
| Aqua | 30-35 |
| Ammonium Acrylates Copolymer | 1-3 |
| CI 77499 (and) Glycerin (and) Aqua (and) Xanthan Gum (and) Sodium Citrate | 8-14 |
| Acrylates/ethylhexyl acrylate copolymer (and) Acrylates dimethylaminoethyl methacrylate copolymer | 30-35 |
| Phenoxyethanol (and) Ethylhexylglycerin (and) Chlorphenesin | 0.9-1.1 |
| Fragrance | 10-20 |
| Total | 100 |

Methods

Drying: in exemplary procedures, the formulae (the tested products) were applied on an area of a skin of an adult. After 2-5 minutes, a finger was gently laid on the applied area for 10 seconds, and then the finger was removed, checking for a residue thereupon. The formulae that exhibited a short drying period (within 5 min) were selected.

Stickiness: in additional exemplary procedures, the formulae were applied on an area of a skin of an adult and then a finger (or cotton wool, or tissue paper) was gently applied thereon using moderate force, and was thereafter removed. The stickiness was rated on a scale of 0-5 (0 being no stickiness).

Smearing: in additional exemplary procedures, the formulae were applied on an area of a skin of an adult and then a moderate force was applied with a finger, trying to smear the formula outside of edges of the applied area. The formulae that exhibited no smearing outside the borders of the applied area were selected.

Adhesion: in additional exemplary procedures, the formulae were applied on an area of a skin of an adult and then a piece of 100% white cotton fabric was pressed on the applied area using a moderate force. The fabric was then checked for residue of the applied formula. The formulae that exhibited no residue on the fabric were selected.

Seawater durability: in additional exemplary procedures, the formulae were applied on an area of a skin of an adult, and then the applied area was dipped into simulated seawater (a solution of 3.5% w/w NaCl) for 20 minutes. The area was then gently dried off by a tapping towel on applied thereon, while avoiding rubbing. The formulae that exhibited no change in the appearance following these procedures were selected.

General durability: in additional exemplary procedures, the formulae were applied on an area of a skin of an adult, subsequently followed by rubbing the applied area, optionally followed by washing. The pattern of the applied area was thereafter evaluated after 12, 24, 36 and 48 hours. The formulae that exhibited a pattern showing a minimal loss of definition at least 48 hours post application were selected.

Fragrance retention: in additional exemplary procedures, the formulae were applied on an area of a skin of an adult, and then a small diamond stencil was used, checking for presence of fragrance 3, 6, 9, and 12 hours post-application. The formulae that demonstrated maintaining fragrance after 12 hours were selected.

Opacity: in additional exemplary procedures, the formulae were applied on an area of a skin of an adult, and then the applied area was visually inspected after drying, checking for areas where skin is observed through the product. Alternately, the products were applied on a cellulose acetate transparency film and the transparency of the applied areas was evaluated.

Graininess: in additional exemplary procedures, the formulae were applied on an area of a skin of an adult, and the applied area was then visually inspected for grainy appearance. The selected formulae were those providing an applied area characterized by smoothness and no graininess.

Cracking: in additional exemplary procedures, the formulae were applied on an area of a skin of an adult, and then the skin around applied area was squeezed 3 times, followed by visually inspecting for cracks. The selected formulae were those exhibiting no cracks on the applied area, with the applied area remaining smooth.

Color matching: in additional exemplary procedures, the formulae were applied on an area of a skin of an adult, and then color of the applied area was compared to a color standard. The selected formulae were those (when applied on the skin) exhibiting a color which is identical to the color standard.

Fragrance matching: in additional exemplary procedures, the formulae were applied on an area of a skin of an adult, and then fragrance of the applied area was compared to a fragrance standard. The selected formulae were those exhibiting a fragrance (when applied on the skin) which is similar to the fragrance standard.

Edges: in additional exemplary procedures, the formulae were applied on an area of a skin of an adult, and then, the edges of the applied area were tested for bleeding, using a complex stencil. The selected formulae were those exhibiting no bleeding of product around the edges of the applied area.

pH: in additional exemplary procedures, the pH of the formulae was measured. The selected formulae were those having pH 7-8.5.

Appearance: in additional exemplary procedures, the formulae were visually inspected for their appearance, and the selected formulae were those characterized by the liquid-gel form.

Viscosity: in additional exemplary procedures, the formulae were tested for their viscosity using Brookfield RV viscometer, spindle #4, 10 rpm. The selected formulae were those characterized by viscosity of 1500 to 12000 mPas at 25° C.

Density: in additional exemplary procedures, the formulae were tested for their density. The selected formulae were those characterized by a density of 0.975-1.075 g/mL.

Microbiological Test: in additional exemplary procedures, the formulae were tested for their antimicrobial properties (according to standard USP <61>/Ph.Eur2.6.12). The selected formulae were those exhibiting: total count of less than 10 CFU/g; yeasts count of less than 10 CFU/g; molds count of less than 10 CFU/g; no *Staph. aureus*, no *Pseudomonas aeruginosa*, and no *Candida albicans* (CFU: colony forming unit).

Results

The 6 exemplary formulae of the invention were applied to the skin around the arm of an adult user. The ingredients and the properties are summarized herein above.

Table 7 below summarizes the properties of the Formulae 1 to 5 described above in a grading scale of 1 (low quality) to 5 (high quality).

Briefly, Formulae 1 and 4 failed to adhere to the skin strongly. Formula 2 is characterized by being sticky on the skin. Formula 3 was not stable on the skin. Formula 4 is characterized by many grains, is smeared easily but is easily removed from the skin. Formula 5 completely failed to adhere to the skin.

The parameters of Formulae 6 were rated with the highest quality (closest to "5"), only when the concentration of the acrylates was within the range of 20 to 40%, with the optimum being about 30%, by weight.

TABLE 7

Summarized results

| Formula no. | Drying | Seawater durability | General durability | Fragrance retention | Cracking | Edges |
|---|---|---|---|---|---|---|
| 1 | 2 | 2 | 3 | 2 | 1 | 3 |
| 2 | 3 | 4 | 3 | 2 | 2 | 3 |
| 3 | 4 | 3 | 3 | 2 | 3 | 3 |
| 4 | 4 | 2 | 1 | 3 | 1 | 1 |
| 5 | 5 | 3 | 2 | 3 | 1 | 1 |

| Formula no. | Stickiness 1- badly sticks 5- easily sticks | Smearing 1- badly smeared 5- easily smeared | Viscosity 1- high 5- optimal | Graininess 1- many grains; 5- almost no grains | General durability on the skin | Adhesion |
|---|---|---|---|---|---|---|
| 1 | 2 | 1 | 2 | 5 | 2 | 2 |
| 2 | 1 | 2 | 2 | 3 | 2 | 3 |
| 3 | 1 | 2 | 2 | 3 | 2 | 3 |

TABLE 7-continued

Summarized results

| 4 | 2 | 1 | 2 | 5 | 2 | 2 |
| 5 | 1 | 2 | 3 | 5 | 3 | 4 |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A composition comprising:
   (i) an aqueous solution at a concentration of 20 to 40% by total weight of said composition;
   (ii) a fragrance at a concentration of 10 to 25%, by total weight of said composition;
   (iii) an acrylic polymer,
   (iv) a polymeric thickener, and
   (v) a pigment, wherein said acrylic polymer is present at a concentration of 25 to 35%, by total weight of said composition.

2. The composition of claim 1, wherein said polymeric thickener is selected from the group consisting of: xanthan gum, gellan gum, welan gum, guar gum, a carob, a flour, or any combination thereof.

3. The composition of claim 1, wherein said pigment is selected from the group consisting of: organic pigment, inorganic pigment, or a combination thereof.

4. The composition of claim 1, wherein said acrylic polymer is selected from the group consisting of: ethylhexyl acrylate copolymer, dimethylaminoethyl methacrylate, methyl methacrylate, ethyl methacrylate, or any combination thereof.

5. The composition of claim 4, comprising ethylhexyl acrylate copolymer, and dimethylaminoethyl methacrylate.

6. The composition of claim 1, further comprising a preservative, wherein said preservative comprises a material selected from the group consisting of: glycerin or a derivative thereof, ethylhexylglycerin, propylene glycol, butylene glycol, caprylyl glycol, potassium sorbate, aromatic alcohol, or any combination thereof, and wherein said preservative is present at a concentration of 0.6 to 1.1%, by total weight of said composition.

7. The composition of claim 6, wherein said aromatic alcohol is phenoxyethanol.

8. The composition of claim 1, wherein said thickener is present at a concentration of 0.1 to 2%, by total weight of said composition.

9. The composition of claim 1, further comprising an emulsifier, wherein said emulsifier is present at a concentration of from 0.1 to 6%, by total weight of said composition.

10. The composition of claim 1, wherein said pigment is present at a concentration of from 2 to 20%, by total weight of said composition.

11. The composition of claim 1, wherein said fragrance comprises one or more materials selected from the group consisting of: an alcohol, an ether, a nitrile, an aldehyde, an ester, a ketone, a lactone, a thiol, an amine, a schiff-base, a terpene, a cyclic alkene, a cyclic oxide, an oxime, an essential oil, and an aromatic species.

12. The composition of claim 1, further comprising one or more non-aqueous solvents at a concentration of 2 to 5%, by total weight of the composition.

13. The composition of claim 12, wherein said one or more non-aqueous solvents comprise glycerin.

14. The composition of claim 1, wherein said acrylic polymer has a viscosity of 50 to 200 mPas and a density of 0.5 to 2 g/cm$^3$, at 20° C.

15. A method for conferring, enhancing, improving or modifying the odor properties of a body surface, comprising contacting, depositing or treating said body surface with the composition of claim 1, said method further comprising a step of drying said composition deposited on said body surface.

16. A kit for applying a fragrance to a subject, comprising the composition of claim 1, and means for topically applying said composition to a body surface of said subject.

* * * * *